United States Patent
Kundu et al.

(10) Patent No.: US 11,013,731 B2
(45) Date of Patent: May 25, 2021

(54) INTRATUMORAL ADMINISTRATION OF SIROLIMUS FOR TREATMENT OF PROSTATE CANCER

(71) Applicant: SANTEN PHARMACEUTICAL CO., LTD., Osaka (JP)

(72) Inventors: Aishwarya Kundu, Emeryville, CA (US); Cecile Escudero, Emeryville, CA (US); Sreenivasu Mudumba, Emeryville, CA (US)

(73) Assignee: Santen Pharmaceutical Co., Ltd., Osaka (JP)

( * ) Notice: Subject to any disclaimer, the term of this patent is extended or adjusted under 35 U.S.C. 154(b) by 0 days.

(21) Appl. No.: 16/475,655

(22) PCT Filed: Dec. 29, 2017

(86) PCT No.: PCT/JP2017/047408
§ 371 (c)(1),
(2) Date: Jul. 2, 2019

(87) PCT Pub. No.: WO2018/128173
PCT Pub. Date: Jul. 12, 2018

(65) Prior Publication Data
US 2019/0343821 A1    Nov. 14, 2019

Related U.S. Application Data

(60) Provisional application No. 62/443,599, filed on Jan. 6, 2017.

(51) Int. Cl.
| | | |
|---|---|---|
| A61P 35/00 | (2006.01) | |
| A61K 31/453 | (2006.01) | |
| A61K 9/00 | (2006.01) | |
| A61K 31/045 | (2006.01) | |
| A61K 47/32 | (2006.01) | |

(52) U.S. Cl.
CPC .......... *A61K 31/453* (2013.01); *A61K 9/0019* (2013.01); *A61K 31/045* (2013.01); *A61K 47/32* (2013.01); *A61P 35/00* (2018.01)

(58) Field of Classification Search
CPC ...................................................... A61P 35/00
See application file for complete search history.

(56) References Cited

U.S. PATENT DOCUMENTS

2005/0222191 A1   10/2005   Falotico et al.

FOREIGN PATENT DOCUMENTS

| WO | WO-2007/092620 A2 | 8/2007 | |
|---|---|---|---|
| WO | WO-2008/109163 A1 | 9/2008 | |
| WO | WO-2008109163 A1 * | 9/2008 | ........... A61K 31/436 |

OTHER PUBLICATIONS

Deantoni, Edward. "Age-Specific Reference Ranges for PSA in the Detection of Prostate Cancer." Cancernetwork.com. Accessed Aug. 15, 2020. (Apr. 1997). Available from: http://www.cancernetwork.com/view/age-specific-reference-ranges-psa-detection-prostate-cancer/>. (Year: 1997).*
Prostate Cancer Foundation. "What is a Gleason Score?" Accessed Aug. 15, 2020. (Oct. 27, 2016). Available from: < https://www.pcf.org/about-prostate-cancer/diagnosis-staging-prostate-cancer/gleason-score > /. (Year: 2016).*
Strickley, Robert G. "Solubilizing Excipients in Oral and Injectable Formulations." Pharmaceutical Research. (Feb. 2004), vol. 21, No. 2, pp. 201-230. (Year: 2004).*
Amato et al., (2008). "Pilot Study of Rapamycin in Patients with Hormone-Refractory Prostate Cancer," Clin. Genitourin. Cancer, 6(2):97-102.
Armstrong et al., (2010). "A Pharmacodynamic Study of Rapamycin in Men with Intermediate-to High-Risk Localized Prostate Cancer," Clin. Cancer Res., 16(11):3057-3066.
Fagone et al., (2013). "Comparative Study of Rapamycin and Temsirolimus Demonstrates Superimposable Anti-Tumour Potency on Prostate Cancer Cells," Basic Clin. Pharmacol. Toxicol., 112:63-69.
Goldberg et al., (2002). "Intratumoral cancer chemotherapy and immunotherapy: opportunities for nonsystemic preoperative drug delivery," J. Pharm. Pharmacol., 54:159-180.
Imrali et al., (2016). "Rapamycin inhibits prostate cancer cell growth through cyclin D1 and enhances the cytotoxic efficacy of cisplatin," Am. J. Cancer Res., 6(8):1772-1784.
International preliminary report on patentability dated Jul. 18, 2019 for PCT/JP2017/047408, filed on Dec. 29, 2017, 7 pages.
International Search Report dated May 6, 2018 for PCT/JP2017/047408, filed on Dec. 29, 2017, 5 pages.
Morikawa et al., (2012). "Rapamycin enhances docetaxel-induced cytotoxicity in a androgen-independent prostate cancer xenograft model by survivin downregulation," Biochem. Biophys. Res. Commun., 419:584-589.
Shikanov et al., (2009). "Intratumoral Delivery of Paclitaxel for Treatment of Orthotopic Prostate Cancer," J. Pharm. Sci., 98:1005-1014.

\* cited by examiner

*Primary Examiner* — John S Kenyon
(74) *Attorney, Agent, or Firm* — Morrison & Foerster LLP

(57) ABSTRACT

The present disclosure relates to methods of treating prostate cancer by administering an effective amount of sirolimus locally to the prostate of a subject in need thereof. In particular, the present disclosure provides methods of treating prostate cancer by intratumoral injection of a liquid formulation comprising sirolimus in which the amount of sirolimus administered is well above the dosage used for preventing transplant rejection.

19 Claims, 6 Drawing Sheets

● = tumor volume measurement

| Group | Treatment | Dosing Volume | Route | Frequency | Total Doses |
|---|---|---|---|---|---|
| 1 | Vehicle | 5 μl / tumor – loading dose<br>5 μl / tumor – regular dose | I.T. | QW | 4 |
| 2 | RAPAMUNE® | 30 μl / mouse – loading dose<br>10 μl / mouse – regular dose | P.O. | QD | 22 |
| 3 | 2% SRL | 5 μl / tumor – loading dose<br>5 μl / tumor – regular dose | I.T. | QW | 4 |
| 4 | 2% SRL | 5 μl / tumor – loading dose<br>5 μl / tumor – regular dose | I.T. | BIW | 7 |

[Fig. 8]
FIG. 8A FIG. 8B
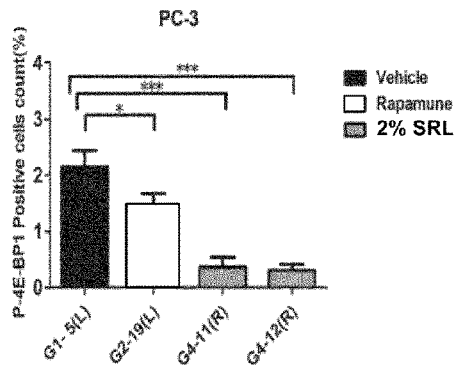 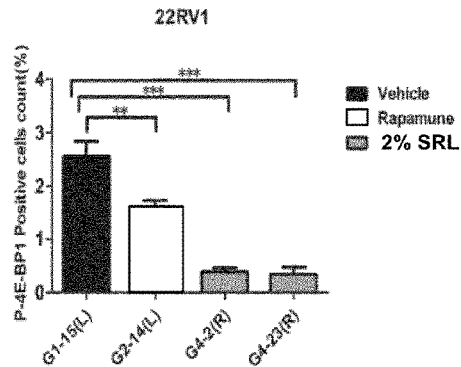
[Fig. 9]
FIG. 9A FIG. 9B
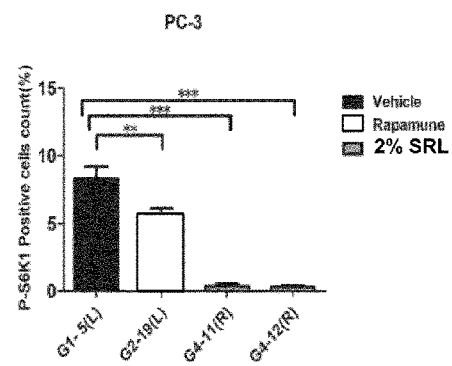 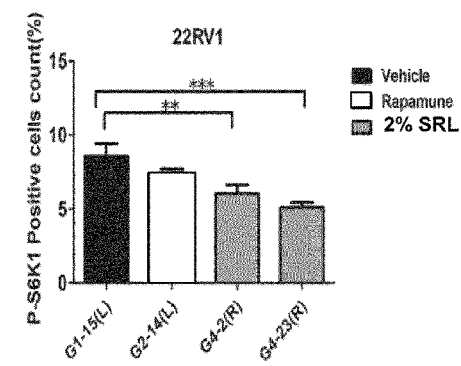
[Fig. 10]
FIG. 10A FIG. 10B
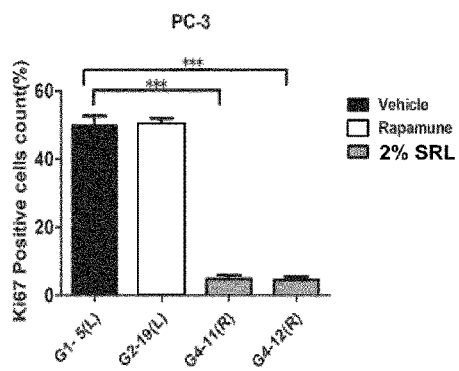 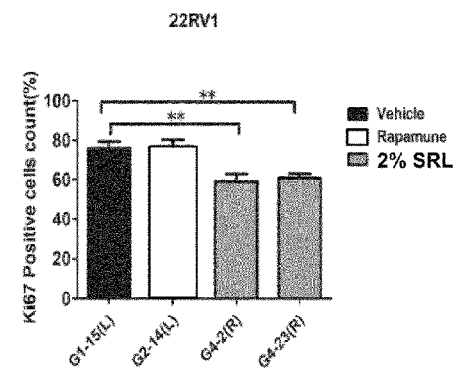

[Fig. 11]
FIG. 11A  FIG. 11B
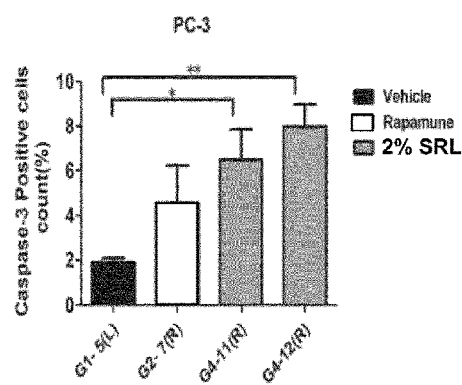 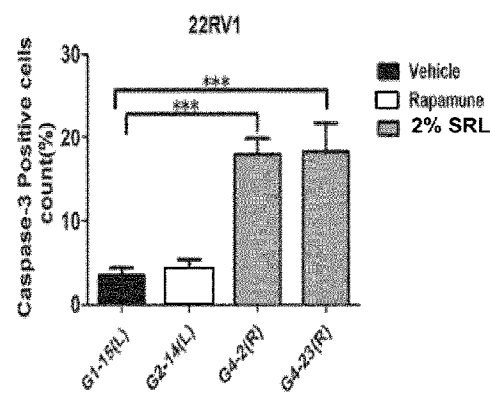
[Fig. 12]
FIG. 12A  FIG. 12B
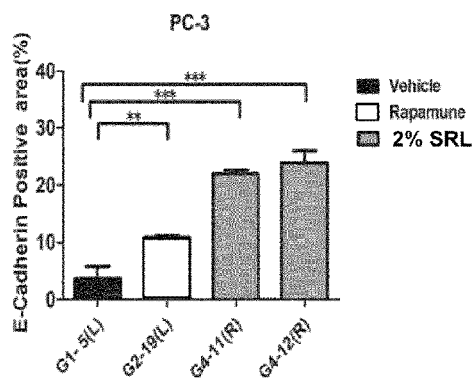 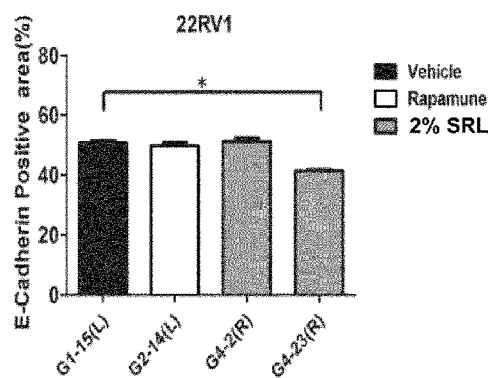

INTRATUMORAL ADMINISTRATION OF SIROLIMUS FOR TREATMENT OF PROSTATE CANCER

CROSS-REFERENCE TO RELATED APPLICATIONS

This application is a U.S. National Phase patent application of International Application No. PCT/JP2017/047408, filed Dec. 29, 2017, which claims benefit of U.S. Provisional Application No. 62/443,599, filed Jan. 6, 2017, each of which is hereby incorporated by reference in in its entirety.

TECHNICAL FIELD

The present disclosure relates to methods of treating prostate cancer by administering an effective amount of sirolimus locally to the prostate of a subject in need thereof. In particular, the present disclosure provides methods of treating prostate cancer by intratumoral injection of a liquid formulation comprising sirolimus in which the amount of sirolimus administered is well above the dosage used for preventing transplant rejection.

BACKGROUND ART

The majority of prostate cancers are adenocarcinomas of the prostate. According to the National Cancer Institute, the median age at prostate cancer diagnosis is 66, and over 180,000 men are predicted to be diagnosed in 2016. Although the five year survival rate is very high for men with localized or regional disease, the survival rate falls to less than 30% for men with metastatic prostate cancer. Currently, prostate cancer is the second leading cause of cancer death in American men.

Many prostate cancers are found during routine screening. Treatment options vary based on cancer stage at diagnosis, age of patient and presence of comorbid conditions. Surgical removal of the prostate (prostatectomy) is commonly employed to cure prostate cancer in the event that the cancer has not metastasized. However, there are significant risks associated with major surgery, such as incomplete tumor removal and resulting recurrence. Additionally, side effects of prostate surgery, such as urinary incontinence, can be debilitating. Other treatment options include radiation, cryotherapy, hormone therapy and chemotherapy. None are ideal, and over time a patient's cancer can become refractory to hormone therapy and resistant to standard chemotherapy agents.

Thus additional, local treatment options are needed as a stand alone or an adjunct to standard of care.

SUMMARY OF INVENTION

The present disclosure provides methods of treating prostate cancer in a mammalian subject (e.g., human male) comprising administering locally to the subject's prostate a liquid formulation comprising an effective amount of sirolimus to treat the prostate cancer, wherein the liquid formulation comprises about 5 mg/ml to about 500 mg/ml sirolimus. In some embodiments, wherein the liquid formulation comprises about 5 mg/ml to about 50 mg/ml sirolimus. In some embodiments, sirolimus administration results in a reduction in volume of the prostate cancer as compared to the volume prior to the treatment. In some embodiments, sirolimus administration inhibits growth of the prostate cancer as compared to the growth as expected in the absence of the treatment. In some embodiments, administering locally comprises intratumoral injection of the liquid formulation. In some embodiments, prostate serum antigen (PSA) level in blood of the subject is less than 4 ng/ml prior to sirolimus administration. In other embodiments, prostate serum antigen (PSA) level in blood of the subject is 4 ng/ml or greater prior to sirolimus administration. In a subset of these embodiments, the PSA level in the blood of the subject is from 4 ng/ml to 10 mg/ml. Alternatively, the PSA level in the blood of the subject is over 10 mg/ml. In some preferred embodiments, sirolimus administration results in a reduction in the PSA level in the blood of the subject as compared to the level prior to the sirolimus administration. In some embodiments, the prostate cancer is detectable by digital rectal exam of the subject prior to the sirolimus administration. In some embodiments, the subject is not a candidate for radical prostatectomy, while in other embodiments the subject is a candidate for radical prostatectomy. The present disclosure provides methods further comprising obtaining a biopsy of the prostate cancer prior to sirolimus administration. In some embodiments, cells of the prostate cancer express mTOR. In some embodiments, cells of the prostate cancer express androgen receptor. In alternative embodiments, cells of the prostate cancer do not express androgen receptor. In some embodiments, the prostate cancer has a Gleason score of from 5 to 7. In other embodiments, the prostate cancer has a Gleason score of or from 8 to 10. In some embodiments, the prostate cancer is a local stage or regional stage cancer. In other embodiments, the prostate cancer is a distant stage cancer. In some embodiments, sirolimus administration is in addition to radiation therapy for the prostate cancer. In some embodiments, sirolimus administration is initiated after the prostate cancer has relapsed following radiation therapy. In some embodiments, sirolimus administration is in addition to androgen deprivation therapy for the prostate cancer. In some embodiments, sirolimus administration is initiated after the prostate cancer has relapsed following androgen deprivation therapy. In some embodiments, the prostate cancer is hormone-refractory prostate cancer. In some embodiments, sirolimus administration is in addition to chemotherapy for the prostate cancer. In a subset of these embodiments, the chemotherapy drug is selected from the group consisting of docetaxel, cabazitaxel, mitoxantrone, estramustine, and combinations thereof. In some embodiments, sirolimus administration is initiated after the prostate cancer has returned following a chemotherapy regimen comprising docetaxel. In some embodiments, the liquid formulation is administered repeatedly on a weekly or biweekly basis. In particular, the liquid formulation may be administered repeatedly for from 2 to 52 weeks per year.

The liquid formulation for treating prostate cancer in a mammalian subject (e.g., human male) by local administration to the subject's prostate comprises about 5 mg/ml to about 500 mg/ml sirolimus, or about 5 mg/ml to about 50 mg/ml sirolimus, or about 10 mg/ml to about 25 mg/ml sirolimus. The liquid formulations of this paragraph are suitable for use in connection with the methods of the preceding paragraph. In some embodiments, the liquid formulation comprises from about 1% to about 35% by weight of sirolimus. In some embodiments, the liquid formulation comprises from 0.5% to 8.0% by weight of sirolimus. In some preferred embodiments, the liquid formulation comprises from 1.0% to 4.0% by weight sirolimus. In some preferred embodiments, sirolimus administration does not result in systemic immunosuppression. In some embodiments, the liquid formulation comprises a polyethylene glycol (PEG). In some embodiments, the PEG is PEG 300 or PEG 400. In some embodiments, the liquid formulation further comprises ethanol. In some preferred embodiments, the liquid formulation comprises about 2.0% (w/w) sirolimus, about 94% (w/w) polyethylene glycol 400 about 4% (w/w) ethanol. In other embodiments, the liquid formulation is a formulation described in Table 2-1. In some embodiments, the liquid formulation comprises PLA. In some embodiments, the liquid formulation comprises DMSO or DMA. In some embodiments, the liquid formulation comprises PLA. In some preferred embodiments, the mammalian subject is human.

BRIEF DESCRIPTION OF DRAWINGS

FIG. 7A shows the effect of test articles on mTOR levels of PC-3 tumor xenograft cells. FIG. 7B shows the effect of test articles on mTOR levels of 22Rv1 tumor xenograft cells.

FIG. 8A shows the effect of test articles on phosphorylated-4E-BP1 levels of PC-3 tumor xenograft cells. FIG. 8B shows the effect of test articles on phosphorylated-4E-BP1 levels of 22Rv1 tumor xenograft cells.

FIG. 9A shows the effect of test articles on phosphorylated-S6K1 levels of PC-3 tumor xenograft cells. FIG. 9B shows the effect of test articles on phosphorylated-S6K1 levels of 22Rv1 tumor xenograft cells.

FIG. 10A shows the effect of test articles on Ki67 expression in PC-3 tumor xenograft cells. FIG. 10B shows the effect of test articles on Ki67 expression in 22Rv1 tumor xenograft cells.

FIG. 11A shows the effect of test articles on cleaved-caspase-3 levels of PC-3 tumor xenograft cells. FIG. 11B shows the effect of test articles on cleaved-caspase-3 levels of 22Rv1 tumor xenograft cells.

FIG. 12A shows the effect of test articles on E-cadherin expression in PC-3 tumor xenograft cells. FIG. 12B shows the effect of test articles on E-cadherin expression in 22Rv1 tumor xenograft cells.

DESCRIPTION OF EMBODIMENTS

Figure 1:
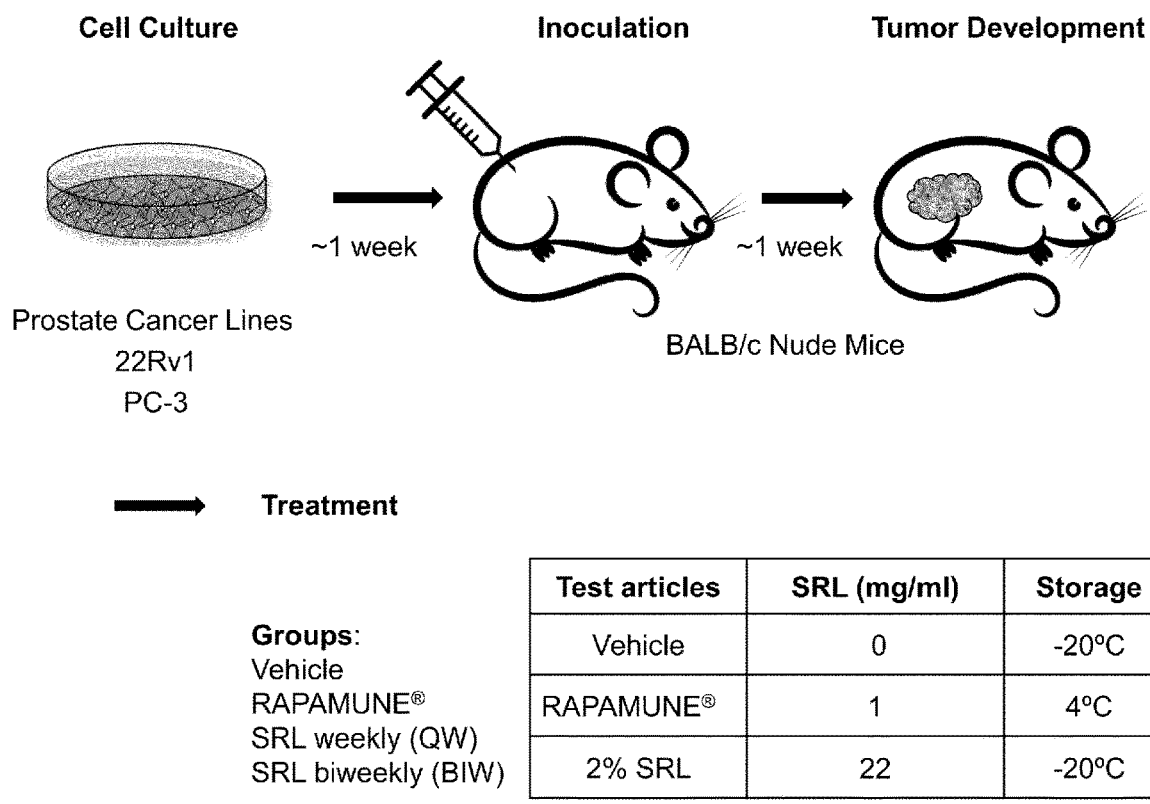
FIG. 1 illustrates the design of the study described in Example 1, which was conducted to compare the efficacy of test articles in the treatment of subcutaneous human prostate cancer xenografts in BALB/c nude mice.

The mechanistic target of rapamycin (mTOR) is a member of the phosphatidylinositol 3-kinase-related kinase family. mTOR is a component of two distinct protein complexes, which play important roles in signaling pathways involved in cell growth, proliferation and survival. Rapamycin (also known as sirolimus) was initially identified as an antifungal agent before it was developed as an immunosuppressant agent. RAPAMUNE (Registered Trademark) (sirolimus oral administration marketed by Wyeth Pharmaceuticals Inc., Philadelphia, Pa.) was approved by the U.S. Food and Drug Administration in 1999 to prevent organ rejection in kidney transplant recipients.

Rapamycin was also found to have anticancer activity against human cancer cell lines (Douros and Suffnes, Cancer Treat Rev, 8:63-87, 1981). Subsequently, rapamycin and its analogs (rapalogs) have been evaluated as anticancer agents in various clinical trials (Yuan et al., J Hematol Oncol, 2:45, 2009; and Dufour et al., Cancers, 3:2478-2500, 2011). The pharmacokinetic profile of oral rapamycin formulations was determined to be undesirable for a chemotherapeutic agent. Thus, several rapalogs have been more extensively evaluated in chemotherapy regimens. TORISEL (Registered Trademark) (temsirolimus kit for injection marked by Wyeth Pharmaceuticals Inc., Philadelphia, Pa.) has been approved to treat advanced renal cell carcinoma (RCC). AFINITOR (Registered Trademark) (everolimus for oral administration marketed by Novartis Pharmaceuticals Corporation, East Hanover, N.J.) has also been approved to treat advanced RCC after failure of treatment with sunitinib or sorafenib, and has been approved to several other cancers alone or in combination with a different class of chemotherapeutic agent.

Up to 80% of prostate cancers were reported to have medium to high levels of mTOR expression as determined by immunohistochemistry using an anti-mTOR antibody. In contrast, normal prostate cancer tissue had only a low level of mTOR expression. This phenotype suggests that mTOR would be a good drug target for prostate cancer. In a small pilot study of rapamycin administered orally to men with hormone-refractory prostate cancer, only one of twelve men had a radiographic response (Amato et al., Clin Genitourin Cancer, 6:97-102, 2008). To date, rapamycin, temsirolimus and everolimus have not been approved to treat prostate cancer.

During development of the present disclosure, sirolimus was found to be a much more potent anticancer agent when administered by intratumoral injection as opposed to oral delivery. Details of two studies in two different mouse models of human prostate cancer are provided in Example 1.

Without being bound by theory, local administration of sirolimus is thought to be advantageous due to poor tissue availability of sirolimus upon systemic administration. In fact, the oral bioavailability of sirolimus is only 14% according to Medscape. Thus, local administration of sirolimus is contemplated to be more effective than systemic administration of sirolimus due to higher tissue availability. Additionally, local administration of sirolimus is expected to minimize deleterious systemic effects (e.g., immunosuppression, hepatic toxicity, renal toxicity, etc.). Specifically, intratumoral injection of sirolimus is not expected to result in increased susceptibility to infection, whereas increased oral administration of sirolimus to achieve the desired prostate tissue availability would likely cause immunosuppression. Levels of sirolimus in the blood of 8 to 10 ng/mL are efficacious in achieving immunosuppression for prevention of kidney transplant rejection. Thus, in preferred embodiments, local administration of sirolimus to the prostate results in levels of sirolimus in the blood below 8-10 ng/mL.

Specifically, the present disclosure provides methods of treating prostate cancer in a mammalian subject (e.g., human male), comprising administering locally to the subject's prostate a liquid formulation comprising an effective amount of sirolimus to treat the prostate cancer, wherein the liquid formulation comprises about 5 mg/ml to about 500 mg/ml sirolimus, or about 5 mg/ml to about 50 mg/ml sirolimus. An exemplary liquid formulation, referred to herein as "SRL" is a solution comprising about 2.0% (w/w) sirolimus, about 94% (w/w) polyethylene glycol (PEG) 400 and about 4% (w/w) ethanol. However, the present disclosure is not limited to the exemplary liquid formulation.

Sirolimus is present in an amount of about 5 mg/ml to about 500 mg/ml, or about 5 mg/ml to about 50 mg/ml in liquid formulations of the present disclosure. In some embodiments, sirolimus is present in an amount greater than (lower limit) 5, 6, 7, 8, 9, 10, 11, 12, 13, 14, 15, 16, 17, 18, 19, 20, 21, 22, 23, 24 or 25 mg/ml. In some embodiments, sirolimus is present in an amount less than (upper limit) 500, 450, 400, 350, 300, 250, 200, 150, 100, 50, 45, 40, 35, 30, 29, 28, 27, 26, 25, 24, 23, 22, 21, 20, 19, 18, 17, 16, 15, 14, 13, 12, 11 or 10 mg/ml. That is, sirolimus is present in an amount in the range between independently selected upper and lower limits.

When expressed as a percent by weight, sirolimus is present at a concentration of from 1% to 35% (w/w) or from 0.5% to 8.0% (w/w) in liquid formulations of the present disclosure. In some embodiments, sirolimus is present at a concentration greater than (lower limit) 1, 2, 3, 4, 5, 6, 7, 8, 9, or 10% (w/w). In other embodiments, sirolimus is present at a concentration greater than (lower limit) 0.5, 0.6, 0.7, 0.8, 0.9, 1.0, 1.1, 1.2, 1.3, 1.4, 1.5, 1.6, 1.7, 1.8, 1.9 or 2.0% (w/w). In some embodiments, sirolimus is present at a concentration less than (upper limit) 35, 30, 25, 20, 15, 14, 13, 12, 11 or 10% (w/w). In other embodiments, sirolimus is present at a concentration less than (upper limit) 8.0, 7.5, 7.0, 6.5, 6.0, 5.5, 5.0, 4.5, 4.0, 3.5, 3.0 or 2.5% (w/w). That is, sirolimus is present at a concentration in the range between independently selected upper and lower limits.

Various formulations comprising concentrations of sirolimus in the range of about 5 mg/ml to about 500 mg/ml sirolimus or about 5 mg/ml to about 50 mg/ml sirolimus are also suitable for use in the methods described herein. Solvents in addition to or instead of one or both of PEG 400 and ethanol may be used in alternative formulations. Additionally, the liquid formulations may comprise an excipient such as antioxidant to increase stability. Moreover, the liquid formulations of the present disclosure are not limited to solutions. In some embodiments, the liquid formulation is a suspension or an in situ gel-forming system.

Suitable solvents for sirolimus include but are not limited to PEG 400, propylene glycol, glycerin, triacetin, diacetin, acetyl triethyl citrate, ethyl lactate, polyglycolated capryl glyceride, ethanol, N-methyl-2-pyrrolidone, gamma-butyrolactone, dimethyl isosorbide, tryethylene glycol dimethyl ether, ethoxy diglycol, glycerol, dimethyl formamide, dimethyl acetamide (DMA), dimethyl sulfoxide (DMSO), benzyl alcohol, and combinations thereof (see, e.g., Simamora et al., Int J Pharmaceutics, 213:25-29, 2001). Water, saline or phosphate buffered saline may also be present. In further aspects, the liquid formulation may contain one or both of a polymethacrylate-based copolymer (see, e.g., Thakral et al., Expert Opin Drug Deliv, 10:131-149, 2013) and polyvinylpyrrolidone. Biodegradable polymers may also be included in vehicles for local administration of sirolimus. In some aspects the biodegradable polymer is a polyester compound. Suitable biodegradable polymers include but are not limited to poly(lactic acid), poly(lactic-co-glycolic acid), polycaprolactone, and combinations thereof. In some aspects, the liquid formulation comprises one or more ingredients selected from the group consisting of DMSO, DMA, DOPC, PLA, trehalose, gellan gum, and water.

DEFINITIONS

As used herein, the term "androgen receptor" refers to a receptor that is activated by binding testosterone or dihydrotestosterone (androgenic hormones). The androgen receptor is also known as the "nuclear receptor subfamily 3, group C, member 4" and "NR3C4." The amino acid sequence of the human androgen receptor is set forth as GenBank Accession No. NP_000035 (isoform 1), and the nucleic acid sequence of the human androgen receptor is set forth as GenBank Accession No. NM_000044 (variant 1).

As used herein, the terms "mechanistic target of rapamycin" and "mTOR" refer to a protein kinase that is the catalytic subunit of mTORC1 and mTORC2, which are involved in various cellular processes. mTOR is also known as "mammalian target of rapamycin," "FK506-binding protein 12-rapamycin-associated protein 1," and "FRAP1." The amino acid sequence of the human mTOR is set forth as GenBank Accession No. NP_004949, and the nucleic acid sequence of the human mTOR mRNA is set forth as GenBank Accession No. NM_004958.

Administration "in combination with" or "in addition to" one or more further therapeutic agents includes simultaneous (concurrent) and consecutive administration in any order.

As used herein, the terms "treating" and "treatment" refer to an approach for obtaining beneficial or desired results, including clinical results. Beneficial or desired clinical results include, but are not limited to, alleviation or amelioration of one or more symptoms, diminishment of extent of disease, stabilized (i.e., not worsening) state of disease, preventing spread of disease, delay or slowing of disease progression, amelioration or palliation of the disease state, and remission (whether partial or total), whether detectable or undetectable. "Treatment" can also mean prolonging survival as compared to expected survival if not receiving treatment. As such, the terms "treating" and "treatment" as used herein, do not require complete alleviation of signs or symptoms, do not require a cure, and specifically include protocols that have a modest effect on the individual.

As used herein and in the appended claims, the singular forms "a," "or," and "the" include plural references unless the context indicates otherwise. For example, "an excipient" includes one or more excipients.

It is understood that aspects and embodiments described herein as "comprising" include "consisting" and/or "consisting essentially of" aspects and embodiments.

The term "about" as used herein in reference to a value describes from 90% to 110% of that value. For instance, about 2% (w/w) sirolimus describes 1.8% to 2.2% (w/w) sirolimus, and include 2.0% (w/w) sirolimus.

EXAMPLES

Abbreviations: BIW (twice per week); HRPC (hormone-refractory prostate cancer); IT or i.t. (intratumoral); PEG (polyethylene glycol); PO or p.o. (oral); PSA (prostate-specific antigen); QD (once per day); QW (once per week); RAPAMUNE (Registered Trademark) (oral sirolimus solution marketed by Wyeth Pharmaceuticals Inc., Philadelphia, Pa.); and SRL (injectable sirolimus solution provided by Santen Inc., Emeryville, Calif.).

Example 1: Treatment of Subcutaneous Human Prostate Cancer Xenografts

This example describes two studies conducted in BALB/c nude mice to test the effect of sirolimus administered systemically (orally) and locally (intratumoral injection). The mice were males of 6-8 weeks of age with body weights in the range of 18-22 grams at the onset of the study. Two phenotypically distinct human prostate carcinoma cell lines were selected for xenograft formation. PC-3 and 22Rv1 are obtainable from ATCC (Registered Trademark) (American Type Culture Collection, Manassas, Va.). The study design is illustrated in FIG. 1.

TABLE 1-1

Prostate Carcinoma Cell Lines

| Cell Line | Androgen Receptor | PSA | ATCC (Registered Trademark) |
|---|---|---|---|
| PC-3 | negative | negative | CRL-1435 |
| 22Rv1 | positive | positive | CRL-2505 |

PC-3 and 22Rv1 tumor cells were maintained in a monolayer culture under standard cell culture conditions. Cells growing in an exponential phase were harvested for tumor inoculation. Each mouse was inoculated at both the left and right flank regions with tumor cells ($1 \times 10^7$) in 0.1 ml of PBS mixed with matrigel (1:1) for tumor development. The treatments were started when the mean tumor size of left or right flank reached about 100-150 mm$^3$.

Before grouping and treatment, all animals were weighed and the tumor volumes were measured every other day using a caliper. Since the tumor volume can impact the effectiveness of any given treatment, tumor volume was used as numeric parameter to randomize selected animals into specified groups. The grouping was performed by using StudyDirector™ software (Studylog Systems, Inc. CA, USA).

The randomized block design was used to assign experimental animals to one of four test groups. First, mice bearing left and right tumors within the initial range were selected and placed into homogeneous blocks according to their right tumor volume. Second, within each block, mice were placed into test groups in a randomized fashion. By using randomized block design to assign mice to test groups, systematic error was minimized. Treatment was initiated immediately after grouping on day 0.

Formulations (test articles) tested include RAPAMUNE (Registered Trademark) (sirolimus solution for oral administration marketed by Wyeth Pharmaceuticals Inc., Philadelphia, Pa.), SRL (sirolimus solution for injection), and Vehicle (no active ingredients). RAPAMUNE (Registered Trademark) contains 1 mg/ml sirolimus, as well as the inactive ingredients phosphatidylcholine, propylene glycol, mono- and diglycerides, ethanol, soy fatty acids, ascorbyl palmitate, polysorbate 90 and ethanol. SRL contains 22 mg/ml sirolimus, polyethylene glycol and ethanol (2% sirolimus, 4% ethanol and 94% PEG 400). Vehicle contains the solvent of SRL (ethanol and PEG 400 without sirolimus).

RAPAMUNE (Registered Trademark) was maintained at 4° C. prior to use. To prepare a loading dose, 180 µl RAPAMUNE (Registered Trademark) was diluted by addition of 2.82 ml sterilized water and to prepare a daily dose, 60 µl RAPAMUNE (Registered Trademark) was diluted by addition of 2.94 ml sterilized water. SRL and Vehicle were stored frozen at −20° C. prior to use. After thawing, SRL and Vehicle were used neat (not diluted).

Figure 2:
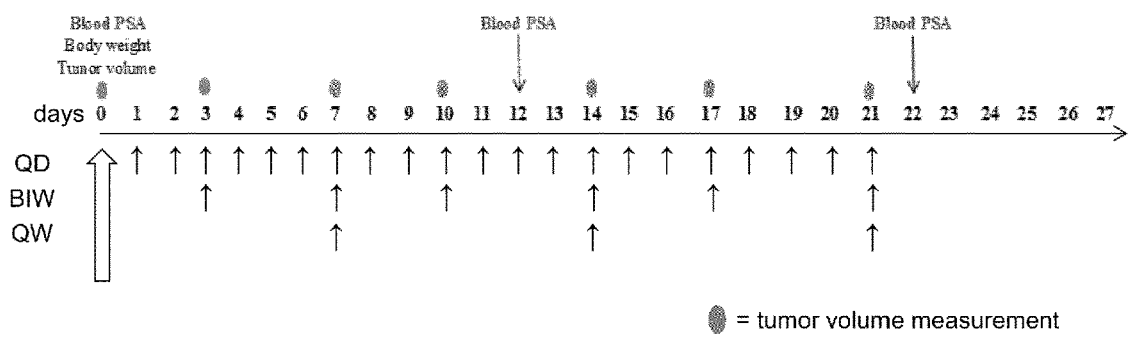
FIG. 2 shows the dosing and data collection schedules of the study described in Example 1.

As shown in FIG. 2, there were four test groups. Each test group contained five mice as follows: 1) Vehicle—5 µl/tumor administered by intratumoral injection on day 0 and 5 µl/tumor QW thereafter; 2) RAPAMUNE (Registered Trademark)—30 µl/mouse administered orally on day 0 (loading dose) and 10 µl/mouse QD thereafter (daily or testing dose); 3) SRL weekly—5 µl/tumor administered by intratumoral injection on day 0 and 5 µl/tumor QW thereafter; and 4) SRL biweekly—5 µl/tumor administered by intratumoral injection on day 0 and 5 µl/tumor BIW thereafter. The RAPAMUNE (Registered Trademark) dosing regimen resulted in administration of 1.8 µg rapamycin orally as a loading dose and administration of 0.2 µg rapamycin orally thereafter as a daily dose to each mouse. The SRL dosing regimen resulted in administration of a dose of 110 µg rapamycin per tumor to each of right and left tumors as both a loading dose and either a weekly or biweekly dose to each mouse.

After tumor cells were inoculated, the mice were checked daily for morbidity and mortality. Body weights and tumor volumes were measured twice weekly. Blood PSA levels were measured on days 0, 12 and 22.

Figure 3A:
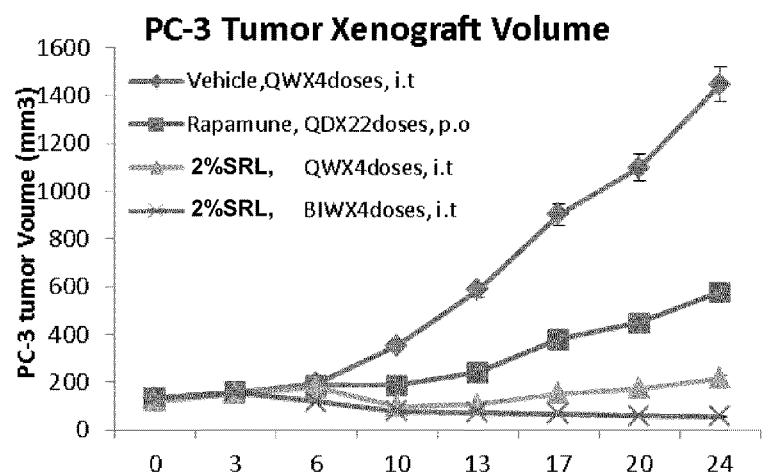
FIG. 3A shows the effect of test articles on the size of PC-3 tumor xenografts in BALB/c nude mice.
Figure 3B:
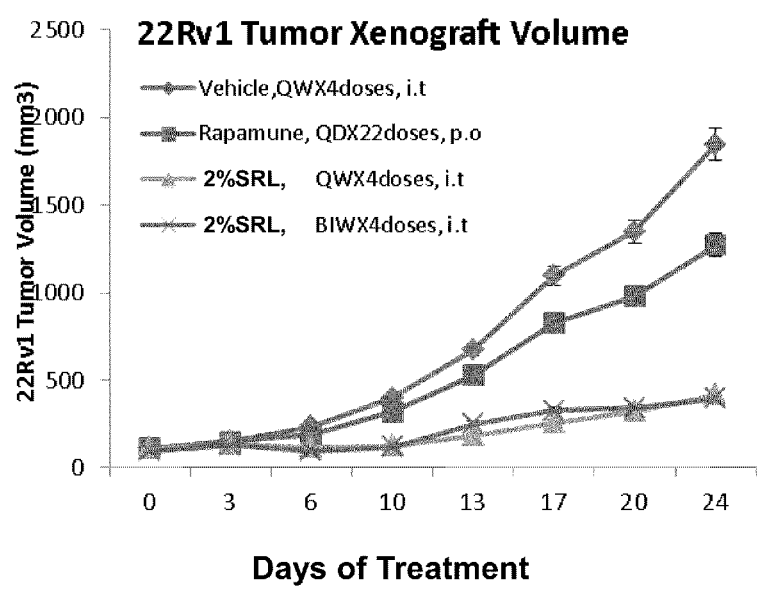
FIG. 3B shows the effect of test articles on the size of 22Rv1 tumor xenografts in BALB/c nude mice.
Figure 5:
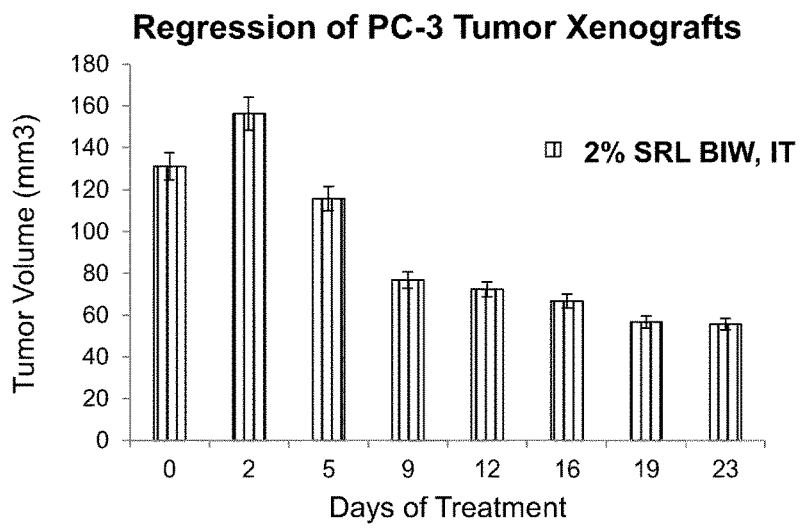
FIG. 5 shows the regression of PC-3 tumor xenografts in BALB/c nude mice treated with a 2% sirolimus formulation administered biweekly by intratumoral delivery.

Tumor volumes were measured in two dimensions using a caliper, and the volume was expressed in cubic millimeters (mm$^3$) using the formula:

$$V = 0.5 a \times b^2$$

where a and b were the long and short diameters of the tumor, respectively. Tumor weight was measured at study termination. The study was terminated when the mean tumor burden (left+right) in each group reached a value of 2000 mm$^3$ or one week after the final dose (day 27). As shown in FIG. 3A-B, intratumoral administration of SRL on a weekly or biweekly basis delayed PC-3 and 22Rv1 xenograft growth to a much greater extent than was observed with oral administration of RAPAMUNE (Registered Trademark) on a daily basis. Importantly, intratumoral administration of SRL on a biweekly basis even resulted in a reduction in the volume of PC-3 xenografts (FIG. 5).

Tumor growth inhibition (TGI), which is an indication of the effectiveness of a treatment regimen, was determined using the following formula:

$$\text{TGI } (\%) = 100 \times (1 - T_{RTV}/C_{RTV})$$

where $T_{RTV}$ and $C_{RTV}$ are the mean relative tumor volume of the treated and control groups, respectively, on a given day.

Figure 4A:
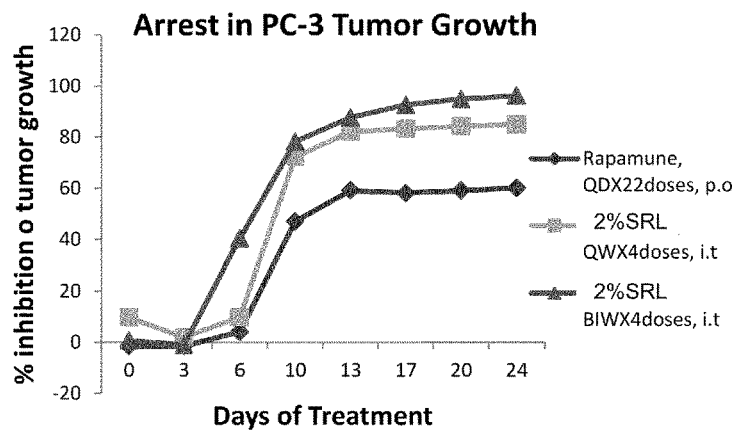
FIG. 4A shows the effect of test articles on the growth of PC-3 tumor xenografts in BALB/c nude mice.
Figure 4B:
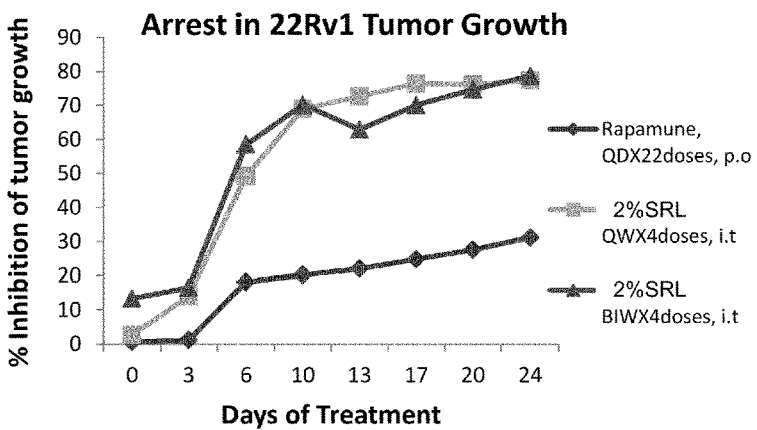
FIG. 4B shows the effect of test articles on the growth of 22Rv1 tumor xenografts in BALB/c nude mice.

RTV (relative tumor volume) was calculated using the following formula:

$$\text{RTV} = V_t / V_0$$

where $V_t$=tumor volume of the drug-treated group on a given day of the study, and $V_0$=tumor volume of the drug-treated group on the initial day of dosing (day 0). As shown in FIG. 4A-B, intratumoral administration of SRL on a weekly or biweekly basis resulted in greater inhibition in PC-3 and 22Rv1 xenograft growth than was observed with oral administration of RAPAMUNE (Registered Trademark) on a daily bases.

Figure 6:
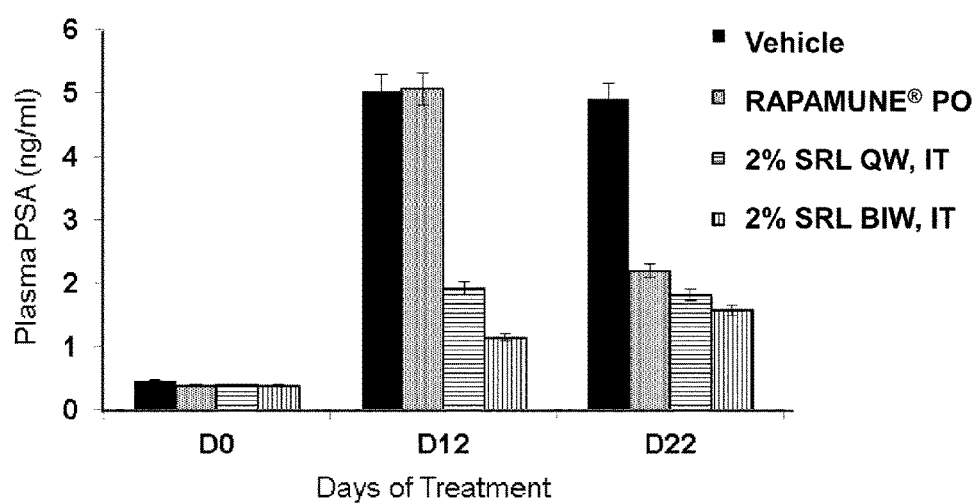
FIG. 6 shows the plasma prostate-specific antigen (PSA) levels in BALB/c nude mice bearing 22Rv1 tumor xenografts.
Figure 6:
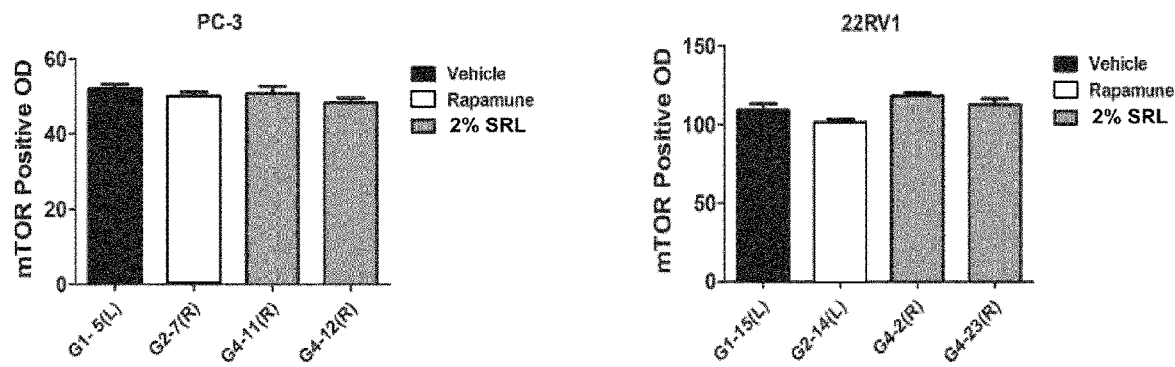

Sirolimus administration to mice bearing 22Rv1 xenografts resulted in a reduction in PSA levels. The reduction in PSA levels occurred more quickly in the mice receiving SRL on a weekly or biweekly basis by intratumoral administration as compared to mice receiving RAPAMUNE (Registered Trademark) on a daily bases (FIG. 6).

In conclusion, locally administered SRL reduced tumor volume in PC3 and 22RV1 xenografted human prostate cancers in nude mice. The reduction in tumor volume was significantly greater than that achieved with orally administered RAPAMUNE (Registered Trademark) in the same models. In addition, locally administered SRL significantly reduced blood PSA levels in 22RV1 xenografted mice and caused regression of PC3 tumors.

The phenotype of residual tumors was subsequently assessed by immunohistochemistry. Specifically, tumors from mice of three groups (vehicle delivered QW IT, RAPAMUNE (Registered Trademark) delivered QD PO, and 2% SRL delivered BIW IT) were harvested upon sacrifice at the end of the study and frozen in liquid nitrogen. The frozen tumors were sectioned and stained with antibodies attached to chromophores or enzymes to permit visualization of antibody binding by standard staining protocols. Staining (brown) was assessed in cells containing nuclei (blue) to rule out non-specific background noise. Statistical analysis of differences among various groups was performed using unpaired t test. P values for all groups were calculated versus the vehicle group, and the differences with a p value <0.05 were considered statistically significant: *p<0.05, p<0.01, *p<0.001.

As expected, levels of mTOR protein within the tumor cells remained unchanged by treatment with RAPAMUNE (Registered Trademark) and 2% SRL, because rapamycin inhibits the kinase activity of mTOR but does not cause its degradation (FIG. 7A-B). In contrast, the levels of phosphorylated downstream targets of mTOR were decreased in tumors of the rapamycin-treated groups. In particular, phosphorylated-eukaryotic translation initiation factor 4E binding protein 1 (p-4E-BP1) levels were considerably lower in tumors from 2% SRL-treated mice than in tumors from RAPAMUNE (Registered Trademark)-treated and vehicle-treated mice (FIG. 8A-B). Levels of phosphorylated-ribosomal protein S6 kinase beta-1 (p-S6K1) were also lower in tumors from 2% SRL-treated mice than in tumors from RAPAMUNE (Registered Trademark)-treated and vehicle-treated mice (FIG. 9A-B). Interestingly, the effect of 2% SRL treatment was more pronounced in mice bearing androgen receptor-negative tumors (PC-3) than in mice bearing androgen receptor-positive tumors (22RV1).

In addition, the impact of rapamycin on molecular markers of tumor cell function was assessed. Levels of Ki-67 were measured to assess tumor cell proliferation. Ki-67 is a nuclear protein that is universally expressed among proliferating cells ($G_1$, S, $G_2$, and mitosis) but is absent in quiescent cells ($G_0$). Levels of Ki-67 were lower in tumors from 2% SRL-treated mice than in tumors from RAPAMUNE (Registered Trademark)-treated and vehicle-treated mice (FIG. 10A-B). It is interesting to note that the effect of 2% SRL treatment on Ki-67 expression was more pronounced in androgen receptor-negative tumors (PC-3) than in androgen receptor-positive tumors (22RV1).

Levels of cleaved caspase-3 (CASP3) were measured to assess tumor cell apoptosis. CASP3 is a member of the cysteine-aspartic acid protease family. CASP3 is a zymogen that is activated in apoptotic cells upon cleavage by an initiator caspases. Levels of cleaved CASP3 were higher in tumors from 2% SRL-treated mice than in tumors from RAPAMUNE (Registered Trademark)-treated and vehicle-treated mice (FIG. 11A-B).

Levels of epithelial-cadherin (E-cadherin) were measured to assess tumor cell metastasis. E-cadherin is a calcium-dependent cell-cell adhesion glycoprotein. Downregulation of E-cadherin decreases cellular adhesion in tissues, which is associated with an increase in cell motility and metastasis. Levels of E-cadherin were higher in tumors from 2% SRL-treated mice than in tumors from RAPAMUNE (Registered Trademark)-treated and vehicle-treated mice (FIG. 12A-B). The effect of 2% SRL treatment on E-cadherin expression was striking in PC-3, which is a grade IV late stage hormone-refractory cell line with high metastatic potential. This indicates that treatment with 2% SRL was able to reestablish the damaged cytoarchitecture by increasing E-cadherin expression. No such effect was observed in the 22Rv1 cell line, which has much lower metastatic potential and hence more intact cytoarchitecture.

In conclusion, a reduced level of downstream mTOR signaling was observed in cells of tumors as a consequence of local administration of SRL. The reduction in downstream mTOR signaling was associated with levels of molecular markers indicative of a decreased cell proliferation, increased apoptosis, and decreased in metastasis. The beneficial reduction in downstream mTOR signaling and tumor cell function was significantly greater than that achieved with orally administered RAPAMUNE (Registered Trademark) in the same models.

Example 2: Sirolimus Formulations

This example describes additional sirolimus formulations for local administration to solid tumors (intratumoral injection). Polylactic acid (PLA) in the formulations of Table 2-1 is poly(D,L-lactide) marketed as RESOMER (Registered Trademark) R 202 H by Evonik Industries AG (Darmstadt, Germany).

TABLE 2

Exemplary Sirolimus Formulations^

| # | SRL | DMSO | DMA | DOPC | Vitamin E | PLA | Trehalose | Gellan gum | WFI |
|---|---|---|---|---|---|---|---|---|---|
| 1 | 8.0 | 18 | — | 36.8 | 36.8 | — | — | — | — |
| 2 | 3.0 | — | 20 | 36.8 | 36.8 | — | — | — | — |
| 3 | 20.0 | — | — | — | — | — | 8 | 0.6 | QS |
| 4 | 32.7 | — | — | — | — | QS | — | — | — |
| 5 | 5.0 | 50 | — | — | — | 45 | — | — | — |
| 6 | 10.0 | 50 | — | — | — | 40 | — | — | — |
| 7 | 5.0 | — | 50 | — | — | 45 | — | — | — |
| 8 | 10.0 | — | 50 | — | — | 40 | — | — | — |

^All ingredients shown as percent by weight (w/w %).
Abbreviations:
(formulation #);
SRL (sirolimus);
DMSO (dimethyl sulfoxide);
DMA (dimethylacetamide);
DOPC (dioleoyl phosphatidyl choline);
PLA (polylactic acid);
WFI (water for injection); and
QS (quantity sufficient).

The invention claimed is:

1. A method of treating prostate cancer in a mammalian subject, comprising administering locally to the subject's prostate a liquid formulation comprising an effective amount of sirolimus to treat the prostate cancer, wherein the liquid formulation comprises about 5 mg/ml to about 500 mg/ml sirolimus.

2. The method of claim 1, wherein sirolimus administration results in a reduction in volume of the prostate cancer as compared to the volume prior to the treatment.

3. The method of claim 1, wherein administering locally comprises intratumoral injection of the liquid formulation.

4. The method of claim 1, wherein prostate serum antigen (PSA) level in blood of the subject is over 4 ng/ml prior to sirolimus administration.

5. The method of claim 4, wherein sirolimus administration results in a reduction in the PSA level in the blood of the subject as compared to the level prior to sirolimus administration.

6. The method of claim 1, further comprising obtaining a biopsy of the prostate cancer prior to sirolimus administration.

7. The method of claim 1, wherein cells of the prostate cancer express mTOR and/or the prostate cancer is hormone-refractory prostate cancer.

8. The method of claim 1, wherein the prostate cancer has a Gleason score of from 5 to 10.

9. The method of claim 1, wherein the prostate cancer is a local stage cancer, a regional stage cancer, or a distant stage cancer.

10. The method of claim 1, wherein sirolimus administration is in addition to radiation therapy, androgen deprivation therapy, and/or chemotherapy for the prostate cancer.

11. The method of claim 1, wherein sirolimus administration is initiated after the prostate cancer has (i) relapsed following radiation therapy, and/or androgen deprivation therapy, or (ii) returned following a chemotherapy regimen comprising docetaxel.

12. The method of claim 1, wherein the liquid formulation is administered repeatedly on a weekly or biweekly basis.

13. The method of claim 12, wherein the liquid formulation is administered repeatedly for from 2 to 52 weeks per year.

14. The method of claim 1, wherein the liquid formulation comprises about 10 mg/ml to about 25 mg/ml sirolimus.

15. The method of claim 1, wherein the liquid formulation comprises from about 0.5% to about 35% by weight of sirolimus.

16. The method of claim 1, wherein the liquid formulation comprises a polyethylene glycol (PEG).

17. The method of claim 16, wherein the liquid formulation further comprises ethanol.

18. The method of claim 1, wherein the liquid formulation comprises about 2.0% (w/w) sirolimus, about 94% (w/w) polyethylene glycol 400, and about 4% (w/w) ethanol.

19. The method of claim 1, wherein the mammalian subject is human.

* * * * *